Figure 1A:
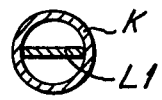

United States Patent [19]

Grimsrud

[11] 4,203,436
[45] May 20, 1980

[54] ASSEMBLY FOR DIVIDING A HOLLOW HYPODERMIC NEEDLE INTO TWO SEPARATED FLOW CONDUITS

[76] Inventor: Lars Grimsrud, P.O. Box 1379, Salmon, Id. 83467

[21] Appl. No.: 891,045

[22] Filed: Mar. 28, 1978

[30] Foreign Application Priority Data

Apr. 5, 1977 [NO] Norway ............................... 771208

[51] Int. Cl.² .............................................. A61M 5/00
[52] U.S. Cl. .............................. 128/214 R; 128/214.4; 128/221
[58] Field of Search ................ 128/214 R, 214.4, 221, 128/2 B, 347, 304

[56] References Cited

U.S. PATENT DOCUMENTS

| | | | |
|---|---|---|---|
| 3,651,926 | 3/1972 | Elfast | 128/2 B X |
| 4,016,879 | 4/1977 | Mellor | 128/214.4 |
| 4,098,275 | 7/1978 | Consalvo | 128/214 R |
| 4,134,402 | 7/1977 | Mahurkar | 128/214 R |

FOREIGN PATENT DOCUMENTS 592193  4/1925  France ................................ 128/214 R Primary Examiner—Dalton L. Truluck

[57] ABSTRACT

A simple and inexpensive assembly is provided for the purpose of dividing any hollow hypodermic needle into two separated flow conduits and connecting each such conduit with an associated pipe coupling means. The main part of said assembly consists of an elongated tongue member having a first portion dimensioned for insertion into the inner cavity of the needle in sealing contact with the cavity wall and a second portion wider than the first portion and designed to protrude from the rear end of the hypodermic needle when the first portion is inserted in said inner cavity. Further, the assembly comprises a pair of pipe stubs for hose connection and shaped for sealing bearing against opposite sides of the protruding second portion of the elongated tongue member and the rear end of the needle, in order to provide flow communication for each pipe stub with an individually associated one of the two separated flow conduits formed by insertion of the first portion of the tongue member into the inner cavity of the needle.

3 Claims, 3 Drawing Figures

ASSEMBLY FOR DIVIDING A HOLLOW HYPODERMIC NEEDLE INTO TWO SEPARATED FLOW CONDUITS

The present invention is related to an assembly for dividing a hollow hypodermic needle into two separated flow conduits and connecting said conduits with associated pipe coupling means for, respectively, discharge of blood for extracorporal treatment from a blood vessel punctured by the needle and returning said blood to the punctured vessel.

Division of hypodermic needles into two concentric flow conduits for the above purpose is previously known from e.g. U.S. Pat. No. 2,474,665. However, with such needles comparatively large dimensions cannot easily be avoided, and thus they may be rather inconvenient to a patient when puncturing a blood vessel. Also, needles of this type are expensive and complicated to manufacture and to sterilize after use. Neither are they fit for use as disposable components, due to said high manufacturing costs.

On this background it is an object of the present invention to provide an assembly designed to accomplish a facile and inexpensive division of any available hollow hypodermic needle in mutually separated flow conduits for the purpose indicated above.

This is achieved in accordance with the present invention by means of an assembly comprising an elongated tongue member having a first portion dimensioned for insertion into the inner cavity of the needle in sealing contact with the cavity wall and a second portion wider than the first portion and designed to protrude from the rear end of the hypodermic needle when the first portion is inserted in said inner cavity, and a pair of pipe stubs for hose connection and shaped for sealing bearing against opposite sides of the protruding second portion of the elongated tongue member and the rear end of the needle, in order to provide flow communication for each pipe stub with an individually associated one of the two separated flow conduits formed by said insertion of the first portion of the tongue member into the inner cavity of the needle.

According to the invention preferably the second portion of the tongue member, said pipe stubs and the rear end of the needle are in whole or in part embedded in a curable mass after the insertion of the first portion of the tongue member into the inner cavity of the needle and mounting the pipe stubs in sealing bearing against the second portion of the tongue member and the rear end of the needle.

Figure 1B:
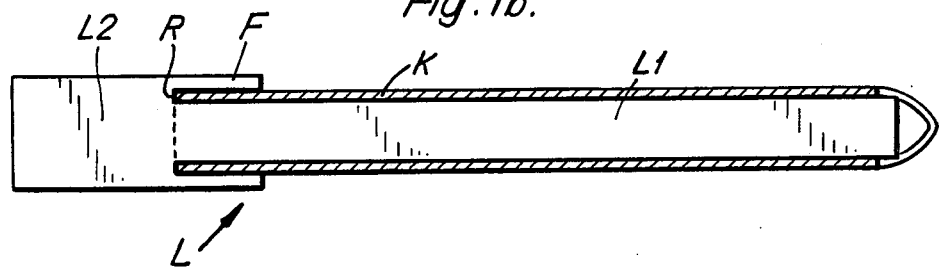
Figure 2:
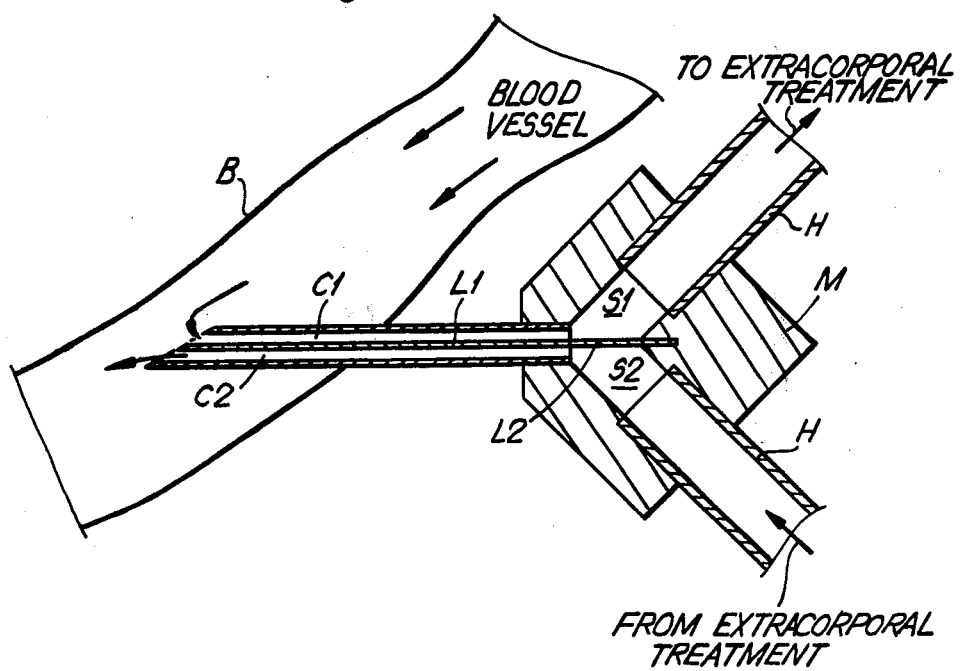

A preferred embodiment of the invention will now be described by way of example and with reference to the accompanying drawings, in which:

FIGS. 1a and 1b show, in cross-section, longitudinal-section, respectively, a hypodermic needle with inserted elongated tongue member according to the invention and FIG. 2 shows in longitudinal section the assembly according to the invention mounted on a conventional hypodermic needle puncturing a blood vessel.

In FIG. 1a it is shown a cross-section of an hypodermic needle K with a portion L1 of an elongated tongue member L inserted along a diameter plane in the inner cavity of the needle, the side edges of said portion L1 being in sealing contact with the cavity wall.

In FIG. 1b the same mounting of the tongue is shown in a longitudinal section of the needle close to the inserted tongue member. It will be apparent that in this mounting position a first portion L1 of the elongated tongue member extends along the whole length of the inner cavity of the needle K, while a wider second portion L2 protrudes from the rear end of the needle, with transverse edges R at the transition between said first and second portions bearing against said rear end. Further each transverse edge R is provided with a lobe F extending parallelly with the first portion L1, the rear end of the needle wall being clasped between said lobes and said first portion of the tongue member.

FIG. 2 shows how the elongated tongue member L may be combined with pipe stubs S1 and S2 providing appropriate flow connections between outer hoses H and the flow conduits C1 and C2 on each side of the tongue portion L1 inserted in the inner cavity of the hypodermic needle K. Said pipe stubs S1 and S2 are shaped to be disposed in sealing bearing against opposite sides of the protruding second portion L2 of the tongue member and the rear end of the needle K. This combination is embedded in a curable mass M to form an integrated unit. The manufacturing costs of this unit will be low, and thus it may be used as a disposable unit to be discarded after single usage.

As shown by the arrows in FIG. 2, blood will be discharged from the punctured blool vessel B through one of the flow conduits C1 of the hypodermic needle K and returned to the blood vessel through the other flow conduit C2 in the needle.

I claim:

1. Assembly for dividing a hollow hypodermic needle into two separated flow conduits and connecting said conduits with associated pipe coupling means for, respectively, discharge of blood for extracorporal treatment from a blood vessel punctured by the needle and returning said blood to the punctured vessel, said assembly comprising an elongated tongue member having a first portion dimensioned for insertion into the inner cavity of the needle in sealing contact with the cavity wall and a second portion wider than the first portion and designed to protrude from the rear end of the hypodermic needle when the first portion is inserted in said inner cavity, a pair of pipe stubs for hose connection and shaped for sealing bearing against opposite sides of the protruding second portion of the elongated tongue member and the rear end of the needle in order to provide flow communication for each pipe stub with an individually associated one of the two separated flow conduits formed by said insertion of the first portion of the tongue member into the inner cavity of the needle, the second portion of the tongue member, said pipe stubs and the rear end of the needle being at least in part embedded in a curable mass after the insertion of the first portion of the tongue member into the inner cavity of the needle and mounting the pipe stubs in sealing bearing against the second portion of the tongue member and the rear end of the needle.

2. Assembly as claimed in claim 1, wherein the transition between said first and second portion of the elongated tongue member is formed by a transverse edge on each side of the tongue member to bear against the rear end of the needle.

3. Assembly as claimed in claim 2, wherein each said transverse edge is provided with a lobe separated from and parallel with the first portion of the tongue member for clasping the rear end of the needle between said lobes and said first portion.

* * * * *